United States Patent [19]

Umezawa et al.

[11] 4,296,106
[45] Oct. 20, 1981

[54] ISTAMYCINS AND PRODUCTION THEREOF

[75] Inventors: Hamao Umezawa; Yoshiro Okami, both of Tokyo; Shinichi Kondo, Yokohama, all of Japan

[73] Assignee: Zaidan Hojin Biseibutsu Kagaku Kenkyu Kai, Tokyo, Japan

[21] Appl. No.: 141,492

[22] Filed: Apr. 18, 1980

[30] Foreign Application Priority Data

May 1, 1979 [JP] Japan .................................. 54/52517
Sep. 17, 1979 [JP] Japan ................................. 54/117912

[51] Int. Cl.³ ...................... A61K 31/71; C07H 15/22
[52] U.S. Cl. ..................................... 424/181; 435/80; 536/17 R
[58] Field of Search ........................... 536/17 R, 17 B; 424/180, 181

[56] References Cited

U.S. PATENT DOCUMENTS 4,205,070  5/1980  Tadanier et al. .................. 536/17 B
4,216,308  8/1980  Iida et al. ........................... 536/17 B

OTHER PUBLICATIONS

Nara, et al., "Jour. Antibiotics", vol. 30, pp. 533-540, 1977.
Okachi, et al., "Jour. Antibiotics", vol. 30, pp. 541-551, 1977.
Egan, et al., "Jour. Antibiotics", vol. 30, pp. 552-563, 1977.
Deushi, et al., "Jour. Antibiotics", vol. 32, pp. 173-179, 187-192, 1979.
Iwasaki, et al., "Jour. Antibiotics", vol. 32, pp. 180-186, 1979.
Okami, et al., "Jour. Antibiotics", vol. 32, pp. 964-966, 1979.
Hotta, et al., "Jour. Antibiotics", vol. 33, 1980, pp. 1502-1509, 1510-1514, 1515-1520.

Primary Examiner—Johnnie R. Brown
Attorney, Agent, or Firm—Richard R. Lloyd

[57] ABSTRACT

Four new antibiotics which are denominated istamycin A, istamycin B, istamycin $A_o$ and istamycin $B_o$, and which are useful as antibacterial agents, are produced by fermentation of a new microorganism, *Streptomyces tenjimariensis*.

7 Claims, 4 Drawing Figures

FIG. 1 INFRARED SPECTRUM OF ISTAMYCIN A HEMI-CARBONATE (KBr PELLET)

INFRARED SPECTRUM OF ISTAMYCIN B HEMI-CARBONATE (KBr PELLET)

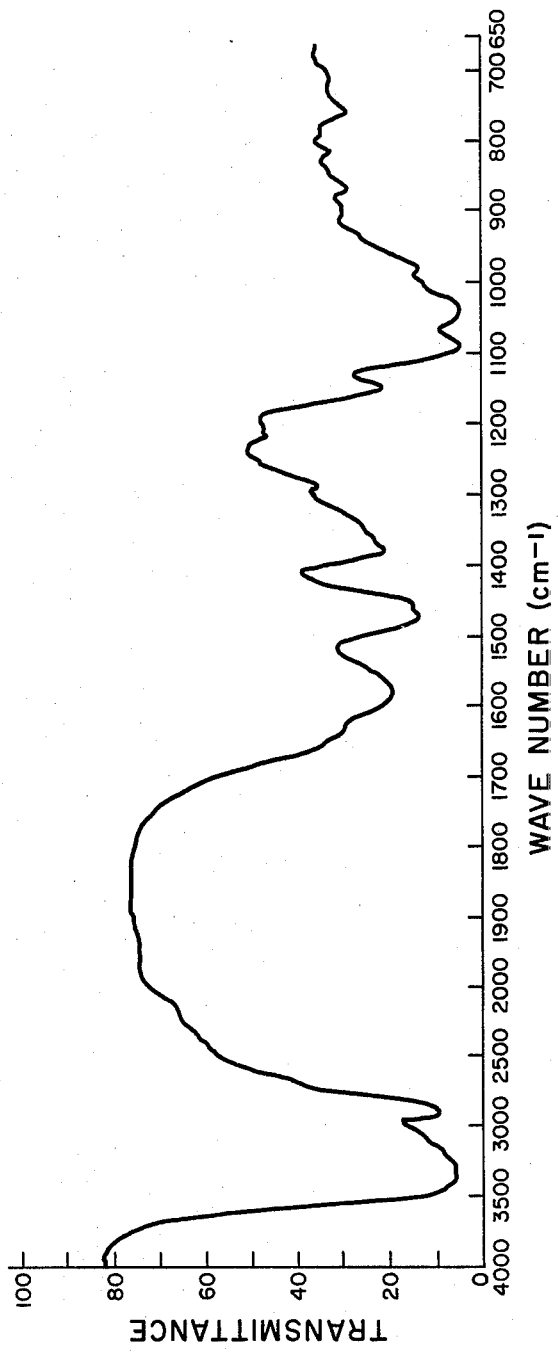

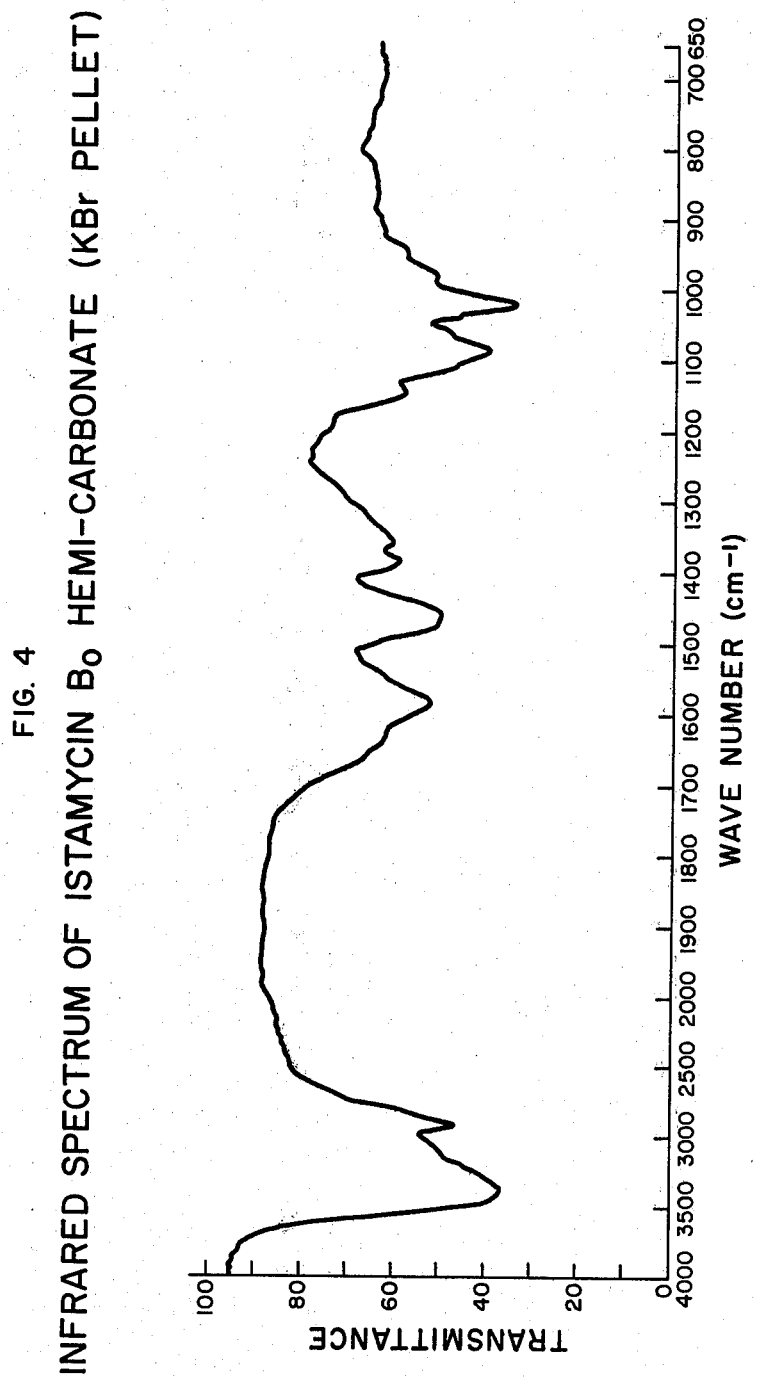

ISTAMYCINS AND PRODUCTION THEREOF

SUMMARY OF THE INVENTION

This invention relates to four new and useful antibiotics designated as istamycin A, istamycin B, istamycin $A_o$ and istamycin $B_o$, respectively. This invention also relates to the fermentative production of these new antibiotics using a new microorganism, *Streptomyces tenjimariensis* (FERM-P 4932, A.T.C.C. 31603), as well as to the uses of these new antibiotics. This invention further relates to the new microorganism itself which is employed in the fermentative production of istamycins.

BACKGROUND OF THE INVENTION

A great variety of pathogenic microorganisms such as bacteria and fungi are causative agents in producing diseases in man, animals and plants. Although a number of antibiotics have been developed, some of which possess usefully high antimicrobial activity against one or more pathogenic microorganisms, there remains a need for more effective therapeutic agents to combat the many diseases caused by such pathogenic microorganisms in man, animals and plants.

An object of this invention is to provide new antibiotics which are useful as antibacterial agents for therapeutic treatment of bacterial infections in man and animals and/or for sterilization of surgical materials and instruments. A further object of this invention is to provide a process for the fermentative production of these new antibiotics. Other objects of this invention will be clear from the following descriptions.

We have done extensive research in an attempt to produce and obtain new and useful antibiotics. As a result, we have now found that when a new strain of the genus Streptomyces which was isolated from a soil sample collected at sea bottom in the coast of the Miura Peninsula in Kanagawa Prefecture, Japan and which was alloted a laboratory designation, Strain No. SS-939 is cultivated in a culture medium under aerobic conditions, four different substances having antibacterial activity against a wide variety of bacteria are produced and accumulated in the culture. We have succeeded in isolating these antibacterial substances from the culture and purifying them. From the chemical, physical and microbiological studies of these isolated substances, it has been confirmed that each of these isolated substances is a new aminoglycosidic antibiotic which has low toxicity and which is distinguishable from any of the known antibiotics. Thus, we have denominated these four new antibiotics as istamycin A, istamycin B, istamycin $A_o$ and istamycin $B_o$, respectively.

DETAILED DESCRIPTION OF THE INVENTION

According to a first aspect of this invention, there is provided as a new antibiotic substance, istamycin which comprises at least one member selected from istamycin A, istamycin B, istamycin $A_o$, istamycin $B_o$ and acid-addition salts thereof;

(a) said istamycin A being characterized by having an empirical formula $C_{17}H_{35}N_5O_5$; containing two N-methyl groups and one O-methyl group in the molecule thereof; showing only end absorption in its ultraviolet absorption spectrum in water; being soluble in water and methanol but sparingly soluble or insoluble in ethanol and other common organic solvents; giving a positive reaction with ninhydrin reagent and Rydon-Smith reagent, giving an Rf value of 0.22 on a cellulose thin layer chromatograph developed with n-butanol-pyridine-acetic acid-water (6:4:2:4 by volume); and the istamycin A hemi-carbonate being in the form of a colorless powder which has no definite melting point but decomposes at 102°–108° C. and gives a specific optical rotation $[\alpha]_D^{25} = +155°$ (c 0.4, water);

(b) said istamycin B being characterized by having an empirical formula $C_{17}H_{35}N_5O_5$; containing two N-methyl groups and one O-methyl group in the molecule thereof; showing only end absorption in its ultraviolet absorption spectrum in water; being soluble in water and methanol but sparingly soluble or insoluble in ethanol and other common organic solvents; giving a positive reaction with ninhydrin reagent and Rydon-Smith reagent; giving an Rf value of 0.25 on a cellulose thin layer chromatograph developed with n-butanol-pyridine-acetic acid-water (6:4:2:4 by volume); and the istamycin B hemi-carbonate being in the form of a colorless powder which has no definite melting point but decomposes at 112°–114° C. and gives a specific optical rotation $[\alpha]_D^{25} = +165°$ (c 0.4, water);

(c) said istamycin $A_o$ being characterized by having an empirical formula $C_{15}H_{32}N_4O_4$; containing two N-methyl groups and one O-methyl group in the molecule thereof; showing only end absorption in its ultraviolet spectrum in water; being soluble in water and methanol but sparingly soluble or insoluble in ethanol and other common organic solvents; giving a positive reaction with ninhydrin reagent and Rydon-Smith reagent; giving an Rf value of 0.36 on a silica gel thin layer chromatograph developed with the lower phase of the mixture of chloroform-methanol-17% aqueous ammonia (2:1:1 by volume); and the istamycin $A_o$ hemi-carbonate being in the form of a colorless crystalline powder which has no definite melting point but decomposes at 111°–114° C. and gives a specific optical rotation $[\alpha]_D^{22} = +76°$ (c 0.56, water);

(d) said istamycin $B_o$ being characterized by having an empirical formula $C_{15}H_{32}N_4O_4$; containing two N-methyl groups and one O-methyl group in the molecule thereof; showing only end absorption in its ultraviolet absorption spectrum in water; being soluble in water and methanol but sparingly soluble or insoluble in ethanol and other common organic solvents; giving a positive reaction with ninhydrin reagent and Rydon-Smith reagent; giving an Rf value of 0.14 on a silica gel thin layer chromatograph developed with the lower phase of the mixture of chloroform-methanol-17% aqueous ammonia (2:1:1 by volume); and the istamycin $B_o$ hemi-carbonate being in the form of a colorless crystalline powder which has no definite melting point and gives a specific optical rotation $[\alpha]_D^{26} = +160°$ (c 1, water).

As used herein, the term istamycin means istamycin A, istamycin B, istamycin $A_o$ or istamycin $B_o$ or a mixture thereof, unless otherwise stated. The term istamycin complex means a mixture of two, three or all of istamycins A, B, $A_o$ and $B_o$ unless otherwise stated. This invention embraces the antibiotics istamycin A, istamycin B, istamycin $A_o$ and istamycin $B_o$ either alone or in a mixture of at least two of these substances, which may be present in a dilute solution, as a crude concentrate, as a crude solid, as a purified solid, as the free base form or in the form of an acid-addition salt with an inorganic or organic acid. Physico-chemical properties of istamycin, including the above-mentioned properties, are given below in more detail.

Istamycin A is a basic compound, and istamycin A isolated as a carbonate thereof is in the form of a colorless powder which has no definite melting point, decomposes at 102°–108° C. and shows a specific optical rotation $[\alpha]_D^{25} = +155°$ (c 0.4, water) and of which an elemental analysis is coincident with the theoretical values of the molecular formula $C_{17}H_{35}N_5O_5 \cdot \frac{1}{2}H_2CO_3$ (C 49.99%, H 8.63%, N 16.65%, O 24.73%). This molecular formula has been confirmed by high-resolution mass-spectrometry (Found: m/e 389.2588; Calcd. for $C_{17}H_{35}N_5O_5$: m/e 389.2635). The infra-red absorption spectrum of istamycin A hemicarbonate pelleted in potassium bromide is shown in FIG. 1 of the attached drawings. The ultraviolet absorption spectrum of istamycin A hemi-carbonate in water shows only end absorption. In the proton ($^1H$) nuclear magnetic resonance absorption spectrum (external standard: TMS, pD 5.4) of istamycin A hemi-carbonate in deutero-water, there are shown characteristic signals at $\delta$ 3.20 (s, N—CH$_3$), 3.57 (s, N—CH$_3$), 3.89 (s, O—CH$_3$), 4.50 (s, CH$_2$) and 5.80 (d, J=3.5 Hz, CH). Istamycin A is soluble in water and methanol but sparingly soluble or insoluble in ethanol and other common organic solvents, and it is positive to the reaction with ninhydrin and to the Rydon-Smith reaction. Istamycin A gives a single spot at Rf 0.22 in a thin layer chromatography on cellulose (Avicel, Funakoshi Yakuhin Co.) developed with mixed solvents of n-butanol-pyridine-acetic acid-water (6:4:2:4 by volume), and it is distinguishable from istamycin B which gives a single spot at Rf 0.25 in the same thin layer chromatography on cellulose as stated hereinafter. In a high-voltage paper electrophoresis (3,300 volts, 15 minutes) using formic acid-acetic acid-water) (25:75:900 by volume), mobility of both istamycin A and istamycin B is 2.15, assuming that the mobility of alanine is 1.0. Accordingly, istamycin A is not distinguishable from istamycin B by high-voltage paper electrophoresis.

Istamycin B is very similar to istamycin A in its properties, and istamycin B is also a basic compound. Istamycin B isolated as a carbonate thereof is in the form of a colorless powder which has no definite melting point, decomposes at 112°–124° C. and gives a specific optical rotation $[\alpha]_D^{25} = +165°$ (c 0.4, water) and of which the elemental analysis is coincident with the theoretical values of the molecular formula $C_{17}H_{35}N_5O_5 \cdot \frac{1}{2}H_2CO_3$ (C 49.99%, H 8.63%, N 16.65%, O 24.73%). This molecular formula has been confirmed by high-resolution mass-spectrometry (Found: m/e 389.2625; Calcd. for $C_{17}H_{35}N_5O_5$: m/e 389.2635). The infra-red absorption spectrum of istamycin B hemicarbonate pelleted in potassium bromide is shown in FIG. 2 of the attached drawings. The ultraviolet absorption spectrum of the istamycin B hemi-carbonate in water shows only end absorption. In the proton ($^1H$) nuclear magnetic resonance absorption spectrum (external standard: TMS, pD 5.4) of istamycin B hemi-carbonate in deutero-water, there are shown characteristic signals at $\delta$ 3.26 (s, N—CH$_3$), 3.59 (s, N—CH$_3$), 3.95 (s, O—CH$_3$), 4.57 (s, CH$_2$) and 5.96 (d, J=3.5 Hz, CH). Like istamycin A, istamycin B is soluble in water and methanol but sparingly soluble or insoluble in ethanol and other common organic solvents, and it is positive to the ninhydrin reaction and to the Rydon-Smith reaction. As stated hereinbefore, istamycin B is separable from istamycin A by thin layer chromatography on cellulose.

Istamycin $A_o$ is also a basic compound, and istamycin $A_o$ isolated as hemi-carbonate thereof is in the form of a colorless crystalline powder which has no definite melting point, decomposes at 111°–114° C. and gives a specific optical rotation $[\alpha]_D^{22} = +76°$ (c 0.56, water) and of which the elemental analysis is coincident with the theoretical values of the molecular formula $C_{15}H_{32}N_4O_4 \cdot \frac{1}{2}H_2CO_3$ (C 51.22%, H 9.15%, N 15.42%). This molecular formula has been confirmed by high-resolution mass-spectrometry (Found: m/e 332.2414; Calcd. for $C_{15}H_{32}N_4O_4$: m/e 332.2420). The infra-red absorption spectrum of the istamycin $A_o$ hemicarbonate pelleted in potassium bromide is shown in FIG. 3 of the attached drawings. The ultraviolet absorption spectrum of istamycin $A_o$ hemi-carbonate in water shows only end absorption. In the proton ($^1H$) nuclear magnetic resonance absorption spectrum (external standard: TMS, pD 5.0) of istamycin $A_o$ hemi-carbonate in deutero-water, there are shown characteristic signals at $\delta$ 3.23 (s, N—CH$_3$), 3.28 (s, N—CH$_3$), 3.94 (s, O—CH$_3$), and 5.86 (d, J=4 Hz, CH). Istamycin $A_o$ is soluble in water and methanol but sparingly soluble or insoluble in ethanol and other common organic solvents, and it is positive in the reaction with ninhydrin and in the Rydon-Smith reaction. Istamycin $A_o$ gives a single spot at Rf 0.36 in a thin layer chromatography on silica gel developed with the lower phase of the mixture of chloroform-methanol-17% aqueous ammonia (2:1:1 by volume). In a high-voltage paper electrophoresis (3,300 volts, 15 minutes) using formic acid-acetic acid-water (1:3:36 by volume), the relative mobility of istamycin $A_o$ is 2.35, assuming that the mobility of alanine is 1.0.

Istamycin $B_o$ is also a basic compound, and istamycin $B_o$ isolated as hemi-carbonate thereof is in the form of a colorless crystalline powder which has no definite melting point and gives a specific optical rotation $[\alpha]_D^{26} = +160°$ (c 1, water) and of which the elemental analysis is coincident with the theoretical values of the molecular formula $C_{15}H_{32}N_4O_4 \cdot \frac{1}{2}H_2CO_3 \cdot \frac{1}{2}H_2O$ (C 49.98%, H 9.20%, N 15.04%). This molecular formula has been confirmed by high-resolution mass-spectrometry (Found: m/e 332.2384; Calcd. for $C_{15}H_{32}N_4O_4$: m/e 332.2421). The infra-red absorption spectrum of istamycin $B_o$ hemi-carbonate pelleted in potassium bromide is shown in FIG. 4 of the attached drawings. The ultraviolet absorption spectrum of istamycin $B_o$ hemi-carbonate in water shows only end absorption. In the proton ($^1H$) nuclear magnetic resonance absorption spectrum (external standard: TMS, pD 5.2) of istamycin $B_o$ hemi-carbonate in deutero-water, there are shown characteristic signals at $\delta$ 3.21 (s, N—CH$_3$), 3.28 (s, N—CH$_3$), 3.91 (s, O—CH$_3$) and 5.92 (d, J=3.5 Hz, CH). Istamycin $B_o$ is soluble in water and methanol but sparingly soluble or insoluble in ethanol and other common organic solvents, and it is positive in the ninhydrin reaction and in the Rydon-Smith reaction. Istamycin $B_o$ gives a single spot at Rf 0.14 in the above-mentioned thin layer chromatography on silica gel developed with the lower phase of the mixture of chloroform-methanol-15% aqueous ammonia (2:1:1 by volume). In the high-voltage paper electrophoresis described above for istamycin $A_o$, istamycin $B_o$ is not distinguishable from istamycin $A_o$ because their mobilities are each 2.35.

From structural studies, the following chemical structure is now submitted by the inventors for istamycin A.

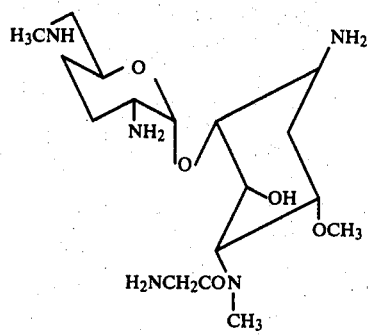

(I)

The following chemical structure is given for istamycin B.

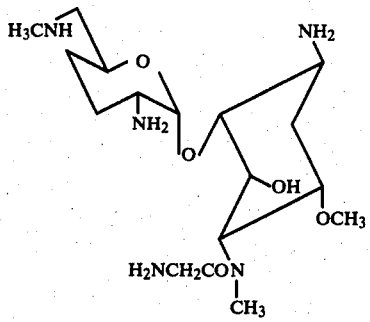

(II)

The following chemical structure is submitted for istamycin $A_o$.

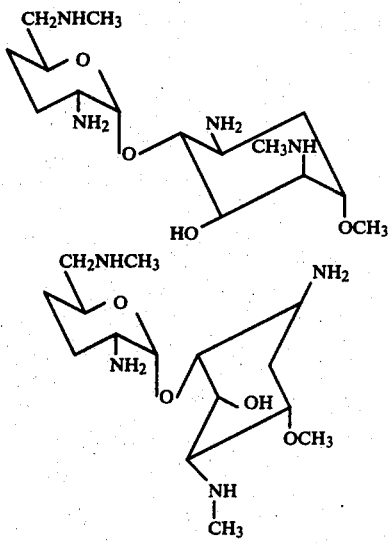

(III)

(IV)

From study of the chemical structure of istamycin $A_o$, it has been found that, in aqueous solution at an alkaline pH, istamycin $A_o$ takes the conformation shown by Formula III, while in aqueous solution at an acidic pH (protonated form), istamycin $A_o$ takes the conformation shown by Formula IV. The following structure is submitted for istamycin $B_o$.

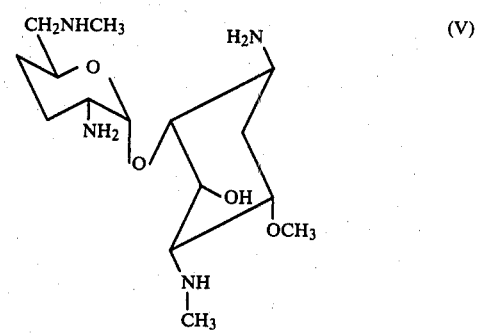

(V)

Istamycin A, istamycin B, istamycin $A_o$ and istamycin $B_o$ each are usually obtained as the free base or a hydrate or a carbonate thereof, and they can be converted into a pharmaceutically acceptable acid-addition salt by reaction with a pharmceutically acceptable acid in a conventional manner. The pharmaceutically acceptable acid-addition salt of istamycin may be those obtained by reacting with an inorganic acid such as hydrochloric acid, hydrobromic acid, sulfuric acid, phosphoric acid, nitric acid or the like, or with an organic acid such as acetic acid, malic acid, citric acid, ascorbic acid, methanesulfonic acid or the like.

Referring to the attached drawings:

FIG. 3 shows the infrared absorption spectrum of a sample of istamycin $A_o$ hemi-carbonate pelleted in potassium bromide.

FIG. 4 shows the infrared absorption spectrum of a sample of istamycin $B_o$ hemi-carbonate pelleted in potassium bromide.

Figure 1:
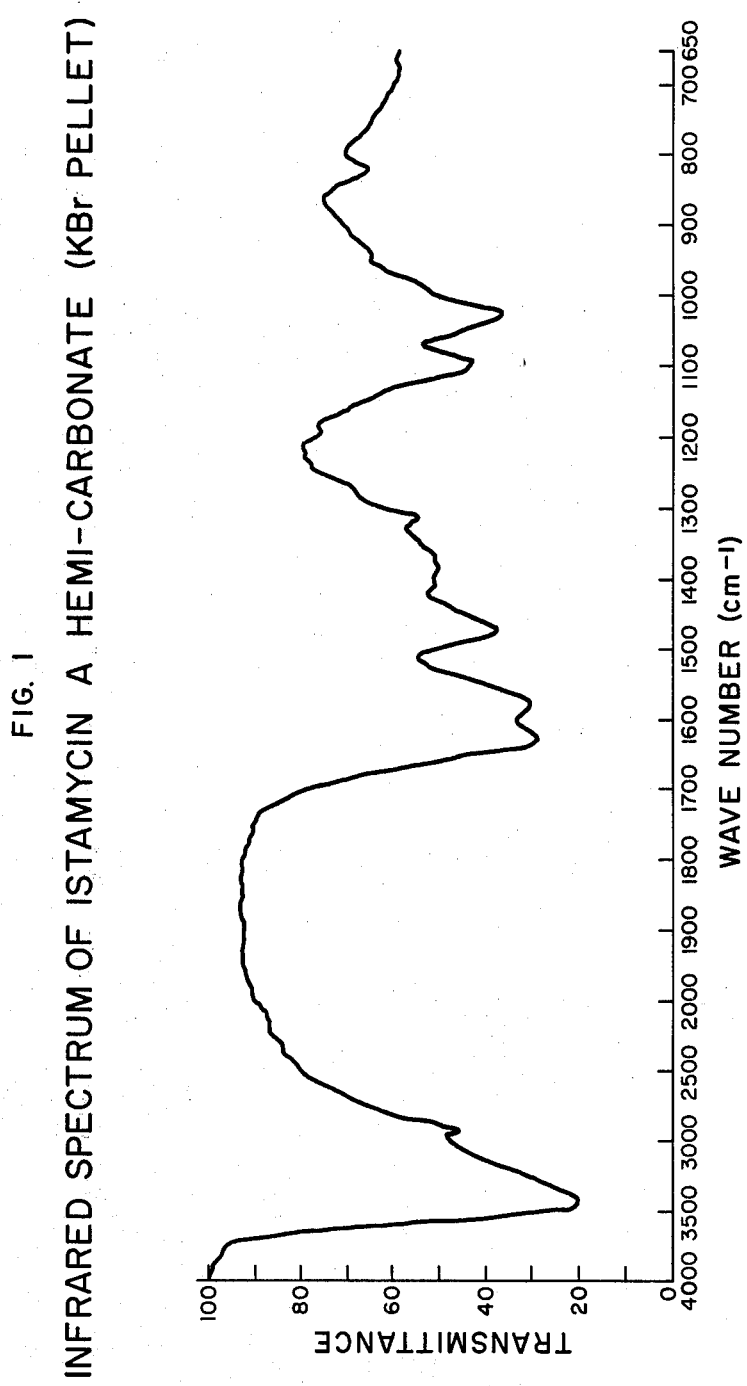
FIG. 1 shows the infrared absorption spectrum of a sample of istamycin A hemi-carbonate pelleted in potassium bromide.
Figure 2:
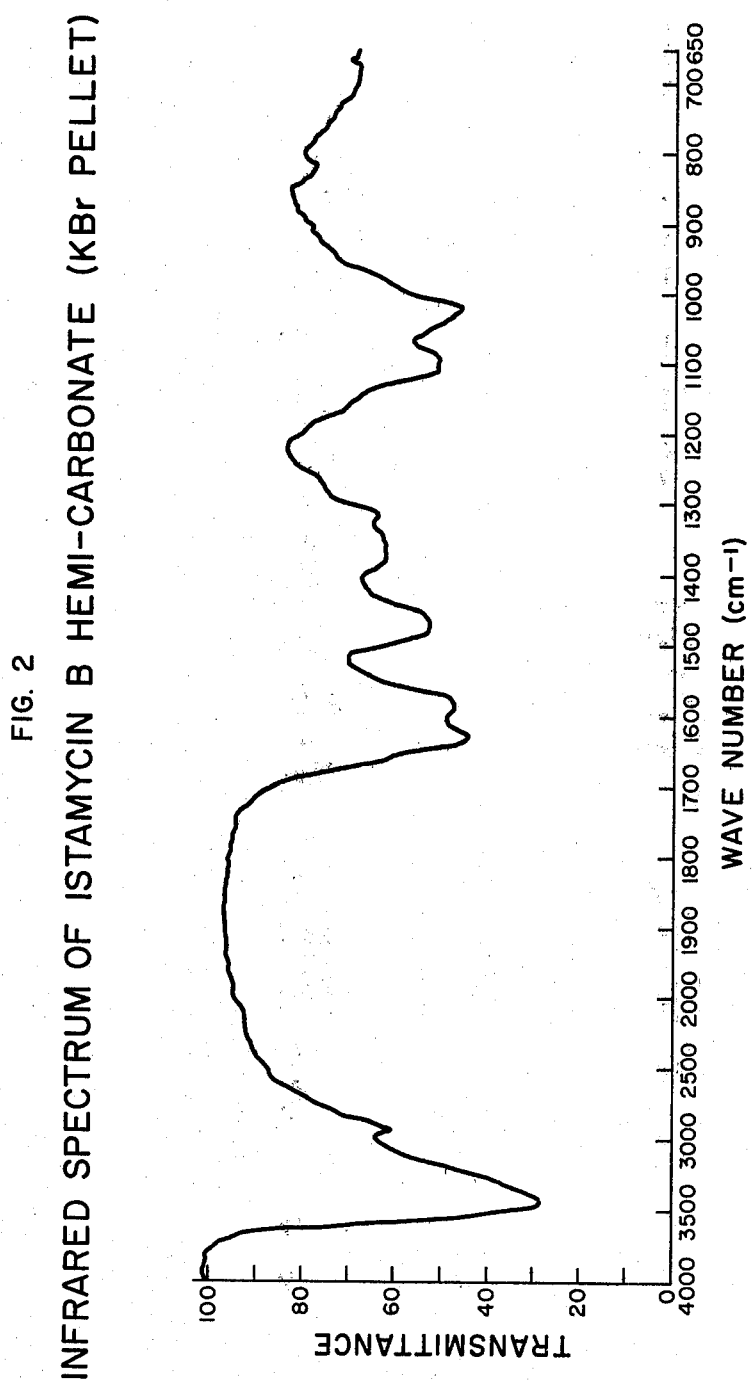
FIG. 2 shows the infrared absorption spectrum of a sample of istamycin B hemi-carbonate pelleted in potassium bromide.

Istamycin A and istamycin B of this invention have high antibacterial activity against a wide range of gram-negative and gram-positive bacteria as will be clear from the antibacterial spectra of these substances shown in Table 1 below. Istamycin A and istamycin B strongly inhibit the growth of gram-negative and gram-positive bacteria. The minimum inhibitory concentrations (mcg/ml) of istamycin A and istamycin B against various bacteria have been determined according to a standard serial dilution method on nutrient agar plates which were incubated at a temperature of 37° C. for 17 hours.

TABLE 1

| Test Microorganisms | Minimum Inhibitory Concentrations (mcg/ml) | |
|---|---|---|
| | Istamycin A | Istamycin B |
| Staphylococcus aureus 209P | 1.56 | 0.78 |
| Staphylococcus aureus Smith | 0.39 | <0.10 |
| Staphylococcus aureus Ap01 | 1.56 | 1.56 |
| Staphylococcus epidermidis 109 | 1.56 | 1.56 |
| Micrococcus flavus FDA 16 | 25 | 6.25 |
| Sarcina lutea PCI 1001 | 1.56 | 3.13 |
| Bacillus anthracis | 0.78 | <0.10 |
| Bacillu subtilus PCI 219 | 0.39 | <0.10 |
| Bacillu subtilis NRRLB-558 | 1.56 | <0.10 |
| Bacillus cereus ATCC 10702 | 6.25 | 3.13 |
| Corynebacterium bovis 1810 | 3.13 | 1.56 |
| Mycobacterium smegmatis ATCC 607 | 1.56 | 0.78 |

TABLE 1-continued

| Test Microorganisms | Minimum Inhibitory Concentrations (mcg/ml) | |
|---|---|---|
| | Istamycin A | Istamycin B |
| *Escherichia coli* NIHJ | 3.13 | 1.56 |
| *Escherichia coli* K-12 | 3.13 | 1.56 |
| *Escherichia coli* K-12 R5 | 6.25 | 6.25 |
| *Escherichia coli* K-12 R388 | 3.13 | 1.56 |
| *Escherichia coli* K-12 J5R11-2 | 3.13 | 1.56 |
| *Escherichia coli* K-12 ML1629 | 3.13 | 3.13 |
| *Escherichia coli* K-12 ML1630 | 6.25 | 3.13 |
| *Escherichia coli* K-12 ML1410 | 12.5 | 3.13 |
| *Escherichia coli* K-12 ML1410 R81 | 6.25 | 3.13 |
| *Escherichia coli* K-12 LA290 R55 | 6.25 | 3.13 |
| *Escherichia coli* K-12 LA290 R56 | 3.13 | 1.56 |
| *Escherichia coli* K-12 LA290 R64 | 3.13 | 1.56 |
| *Escherichia coli* W677 | 3.13 | 1.56 |
| *Escherichia coli* JR66/W677 | 6.25 | 6.25 |
| *Escherichia coli* K-12 C600 | | |
| *Escherichia coli* R135 | >50 | 25 |
| *Escherichia coli* JR225 | 3.13 | 1.56 |
| *Klebsiella pneumoniae* PCI602 | 6.25 | 3.13 |
| *Klebsiella pneumoniae* 22#3038 | 12.5 | 12.5 |
| *Shigella dysenteriae* JS11910 | 12.5 | 6.25 |
| *Shigella flexneri* 4B JS11811 | 12.5 | 12.5 |
| *Shigella sonnei* S11756 | 12.5 | 12.5 |
| *Salmonella typhi* T-63 | 1.56 | 12.5 |
| *Salmonella enteridtidis* 1891 | 3.13 | 3.13 |
| *Proteus vulgaris* OX19 | 1.56 | 0.78 |
| *Proteus rettgeri* GN311 | 25 | 12.5 |
| *Proteus rettgeri* GN466 | 6.25 | 6.25 |
| *Serratia marcescens* | 25 | 12.5 |
| Serratia SOU | >50 | >25 |
| Serratia 4 | >50 | >25 |
| Providencia Pv16 | 50 | 12.5 |
| Providencia 2291 | 50 | 25 |
| *Pseudomonas aeruginosa* A3 | >50 | 12.5 |
| *Pseudomonas aeruginosa* No. 12 | >50 | >25 |

The antibacterial activity of istamycin $A_o$ and istamycin $B_o$ are determined according to a standard serial dilution method on nutrient agar plates in the same manner as for istamycin A and istamycin B, but show very weak activity. It has been found that the antibacterial activity of istamycin $A_o$ is about 1/200 that of istamycin A and the antibacterial activity of istamycin $B_o$ is also about 1/200 that of istamycin B when using *Bacillus subtilis* as the test microorganism.

The acute LD$_{50}$ values of istamycin A, istamycin B, istamycin $A_o$ and istamycin $B_o$ in mice by intravenous injection were greater than about 100/mg/kg.

In view of the above-mentioned properties of istamycins A and B, it is seen that istamycins A and B are similar in some points to fortimicin A [R. Okachi et al., Journal of Antibiotics Vol. 30, Page 541 (1977)] and sporaricin [T. Deushi et al., Journal of Antibiotics Vol. 32, Page 173 (1979)]. Nonetheless, it is confirmed that istamycins A and B are undoubtedly distinguished from these known antibiotics in that the istamycins do not contain the C-methyl group but contain two N-methyl groups in the molecule thereof, so that istamycins A and B and hence istamycins $A_o$ and $B_o$ are new antibiotic substances.

According to a second aspect of this invention, there is provided a process for the production of the antibiotic istamycin complex, which comprises cultivating an istamycin-producing strain of Streptomyces under aerobic conditions in a culture medium containing assimilable sources of carbon and nitrogen until a substantial amount of istamycin is produced and accumulated in the culture medium. The process of this second aspect of the invention may also include the step of recovering the istamycin complex from the culture medium. By the term istamycin complex is herein meant a mixture of two, three or all four of istamycins A, B, $A_o$ and $B_o$.

According to one embodiment of the second aspect of the invention, there is provided a process of producing istamycin A which comprises cultivating an istamycin A-producing strain of Streptomyces under aerobic conditions in a culture medium containing assimilable sources of carbon and nitrogen until istamycin A is produced and accumulated by said microorganism in the culture medium. According to another embodiment of the second aspect of the invention, there is provided a process of producing istamycin B which comprises cultivating an istamycin B-producing strain of Streptomyces under aerobic conditions in a culture medium containing assimilable sources of carbon and nitrogen until istamycin B is produced and accumulated by said microorganism in the culture medium. According to a further embodiment of the second aspect of the invention, there is provided a process of producing istamycin $A_o$ which comprises cultivating an istamycin $A_o$-producing strain of Streptomyces under aerobic conditions in a culture medium containing assimilable sources of carbon and nitrogen until istamycin $A_o$ is produced and accumulated by said microorganism in the culture medium. According to still another embodiment of the second aspect of the invention, there is provided a process of producing istamycin $B_o$ which comprises cultivating an istamycin $B_o$-producing strain of Streptomyces under aerobic conditions in a culture medium containing assimilable sources of carbon and nitrogen until istamycin $B_o$ is produced and accumulated by said microorganism in the culture medium. The process according the second aspect of the invention may include the step of recovering the istamycin A, istamycin B, istamycin $A_o$, istamycin $B_o$ or a mixture of at least two of them, either in crude or pure form, and either as a solid or a solution.

As an example of the istamycin-producing strain, there is mentioned a strain of actinomycetes which was isolated by the present inventors from a soil sample collected from the sea bottom on the coast of Miura Peninsula in Kanagawa Prefecture, Japan in August of 1978 and which is designated as Strain No. SS-939.

This SS-939 strain has the following microbiological properties.

(a) Microscopical morphology

When the SS-939 strain grows well in agar medium, the mycelium produces monopodial branches. Straight or slightly curved aerial hyphae develop from the substrate mycelium. The matured aerial hyphae bear at the tip a chain of 10 to 50 spores. The shape of the spores is cylindrical (1 micron wide×4-5 microns long). No spirals or whorl branching is observed. Under an electron microscope, the surface of the spore is smooth and has no spiny or hairy structure. Neither flagellum nor sporagium is observed, so that the SS-939 strain is a typical strain of Streptomyces.

(b) Cultural characteristics on different culture media (1) On sucrose-nitrate agar medium (incubated at 27° C.): Weak colorless growth with aerial hyphae which are white in color and gradually vary into grey with a bluish-green tinge (17 ec, aqua blue, according to the color standard given in the "Color Harmony Manual" published by Container Corporation of America; the same color standard applies hereinafter unless otherwise stated). No remarkable diffusible pigment is produced in the incubation medium.

(2) On glycerine-asparagine agar medium (incubated at 27° C.): Substantially same as on the sucrose-nitrate agar medium as stated in the above (1) but aerial hyphae are scantily produced.

(3) On starch agar medium (incubated at 27° C.): Substantially same as on the sucrose-nitrate agar medium as stated in the above (1) but aerial hyphae are produced.

(4) On tyrosine agar medium (incubated at 37° C.): Cultural characteristics substantially same as on the media indicated in the above (1) and (2) are observed, but malanoid pigment is produced.

(5) On nutrient agar medium (incubated at 27° C.): Colorless growth on which aerial hyphae of white color are formed. The incubation medium is tinged with dark brown.

(6) On yeast extract-malt extract agar medium (incubated at 27° C.): Colorless growth on which aerial hyphae are formed. The aerial hyphae are of white color and gradually shows grey with bluish-green tinge (19 dc, aqua green). The medium becomes dark brown in color.

(7) On oat-meal agar medium (incubated at 27° C.): Colorless growth on which aerial hyphae with white to bluish-grey color (17 ec, aqua blue) are formed.

(c) Physiological properties (1) Temperature for growth: growth at 20°–41° C.

(2) Hydrolysis of starch: starch is hydrolyzed in starch agar medium.

(3) Coagulation and peptonization of skimmed milk: substantially negative.

(4) Formation of melanoid pigment: positive on tyrosine agar medium and on peptone-yeast extract-iron agar medium.

(d) Utilization of carbon sources for growth (estimated in Pridham-Gottlieb medium)

Glucose and inositol only are utilizable.

Arabinose, D-xylose, sucrose, rhamnose, raffinose and D-mannitol are not utilizable. Utilization of D-fructose is doubtful.

Summarizing the above-mentioned characteristics of the SS-939 strain, it is noted that this strain belongs to the genus Streptomyces and is characterized by the absence of spirals on the aerial hyphae and by its chromogenicity. On the basis of the above-mentioned properties, the SS-939 strain is compared with known species of Streptomyces with reference to descriptions in International Streptomyces Project (ISP) and Bergey's Determinative Bacteriology, 1974. Characteristics of the SS-939 strain resemble most closely *Streptomyces viridochromogenes*. However, the SS-939 strain is different from *S. viridochromogenes* in that the SS-939 strain produces neither spirals nor shows utilization of xylose, arabinose, rhamnose, fructose, raffinose or mannitol. Another distinguishable difference between them is that the surface of the spores produced by the SS-939 strain is not spiny. Nextly, *Streptomyces viridifaciens* has no chromogenicity but produces aerial hyphae of a color similar to that of the SS-939 strain. However, they are distinguishable from each other in that the SS-939 strain neither produces spirals at the aerial hyphae nor utilizes fructose or sucrose as the sole carbon source for growth. We have been unable to find any known species of Streptomyces which exhibits the properties of utilization of carbon sources characteristic of the SS-939 strain. Consequently, the SS-939 strain is determined to be a new species and is named *Streptomyces tenjimariensis*.

*Streptomyces tenjimariensis* SS-939 strain was deposited in the Japanese public depository "Fermentation Research Institute," Agency of Industrial Science and Technology, Tsukuba-gun, Ibaragi Prefecture, Japan under the deposit number FERM-P 4932 on and since Apr. 21, 1979, and also was deposited in the American Type Culture Collection, Washington, D.C., U.S.A., under ATCC number 31603.

Mutation of actinomycetes occurs frequently under either artificial or spontaneous conditions. Accordingly, this invention includes the use of the SS-939 strain as well as its variants and mutants as long as these produce istamycin.

Istamycin can be obtained by aerobic cultivation of spores or mycelia of an istamycin-producing strain of Streptomyces, for example, *Streptomyces tenjimariensis* SS-939 strain (identical with FERM-P 4932 or ATCC number 31603). In carrying out the process of the second aspect of this invention, therefore, an amount of spores or mycelia of an istamycin-producing strain is inoculated to a suitable culture medium therefor comprising nutrient sources assimilable by the strain and is then incubated under aerobic conditions until there is obtained a culture broth containing istamycin, that is, at least one of istamycin A, B, $A_o$ and $B_o$. Generally, nutrient constituents of the culture media commonly employed for the cultivation of ordinary actinomycetes can be used for the purpose of this invention. For instance, commercially available soybean meal, peanut powder, cotton seed meal, dried yeast, peptone, meat extract, casein, corn steep liquor, sodium nitrate, ammonium sulfate and the like may be useful as the nitrogen sources. Commercially available carbohydrates such as glucose, starch, glycerine, maltose, dextrin, saccharose, lactose and the like as well as soybean oil and fats are useful as the carbon sources. In addition, inorganic salts such as sodium chloride, calcium carbonate, magnesium sulfate, manganese chloride and phosphates as well as various amino acids can be employed in the culture medium, if required. Any of the nutrient materials which are known for the cultivation of actinomycetes may be used in the process of this invention, as long as it is assimilable by the istamycin-producing strain for the production of istamycin.

For the production of istamycin on a large scale, liquid cultivation is preferred. Any temperature at which the istamycin-producing strain is able to grow and produce istamycin can be adopted for the cultivation, but a preferred temperature is in the range of 25° C. to 30° C. The cultivation is continued for a period of time sufficient to produce and accumulate a sufficient amount of istamycin in the culture medium. The cultivation typically is conducted for 2 to 7 days.

Assays of istamycin A and istamycin B can be made using *Bacillus subtilis* PCI 219 as the test organism according to the standard cup-plate method which has usually been employed for the assay of known antibiotics. A pure sample of istamycin A which was obtained in Example 3, below, was used as an authentic product which exhibited a potency of 1000 mcg (units) per mg. Then, the pure sample of istamycin B which was obtained from the same Example 3 exhibited a potency of 3170 mcg (units)/mg.

Assays of istamycin $A_o$ and istamycin $B_o$ also can be made using *Bacillus subtilis* PCI 219 as the test organism according to the standard cup-plate method which has usually been employed for the assay of known antibiotics. A pure sample of istamycin $A_o$ obtained according to this invention has a potency of 5 mcg (units)/mg and a pure sample of istamycin $B_o$ obtained according to this invention has a potency of 10 mcg (units)/mg, assuming that the pure authentic sample of istamycin A has a potency of 1000 mcg (units)/mg.

Istamycin A, istamycin B, istamycin $A_o$ and istamycin $B_o$ and their acid-addition salts are readily soluble in water, and the istamycin complex is mainly present in solution in the liquid phase of the culture broth. Istamycins A and B as well as istamycin $A_o$ and istamycin $B_o$ in aqueous solution are essentially non-extractable by an organic solvent such as butanol, butyl acetate, chloroform or other water-immiscible organic solvent, so that these organic solvents can be utilized for removal of impurities from the culture broth by extraction, if necessary. For the recovery of istamycin complex from the culture broth or from an aqueous solution of istamycin, the culture broth or the aqueous solution may be treated with various adsorbents to separate istamycin therefrom by adsorption. When activated carbon is used as the adsorbent, the istamycin which is adsorbed by the carbon may be extracted by treatment with weakly acidified water, weakly acidified aqueous methanol, weakly acidified aqueous propanol, weakly acidified aqueous acetone or the like.

Istamycin, owing to its basicity may efficiently be adsorbed by a cation-exchange resin, from which istamycin may then be eluted with a suitable solvent. The adsorption on a cation-exchange resin is a most suitable way of recovering istamycin from a large volume of the culture broth. The cation-exchanger available for this purpose may be a cation-exchange resin comprising carboxylic functions such as Amberlite IRC-50 and Amberlite CG-50 (a product of Rohm & Haas Co., U.S.A.), Lewatit CNP (a product of Bayer Co., West Germany) or CM-Sephadex (a product of Pharmacia Co., Sweden) in their $H^+$ form, $Na^+$ form or $NH_4^+$ form, or a mixture of these forms. The istamycin which has been absorbed by the cation-exchanger can efficiently be eluted therefrom by treating with acidified water, diluted aqueous ammonia or an aqueous solution of an inorganic salt. For the elution to this end, 0.2 N to 1 N hydrochloric acid and 0.2 N to 1 N aqueous ammonia are suitable. As istamycin A and istamycin B as well as istamycin $A_o$ and istamycin $B_o$ are essentially non-adsorbable by an anion-exchange resin, an anion-exchange resin can be employed to neutralize an acidic aqueous solution of istamycin or to remove acidic impurities from the solution of istamycin.

In order to obtain istamycin A, istamycin B, istamycin $A_o$ and istamycin $B_o$ separately from the istamycin complex thus recovered, the istamycin complex is subjected to column chromatography on silica gel developed with the lower phase composed of chloroform-methanol-17% aqueous ammonia (2:1:1 by volume) or some analogous mixed solvents, by utilizing the characteristics of istamycins that istamycin A gives a single spot at Rf 0.17, istamycin B gives a single spot at Rf 0.11, istamycin $A_o$ gives a single spot at Rf 0.36 and istamycin $B_o$ gives a single spot at Rf 0.14 in a silica gel thin layer chromatography developed with the lower phase of the mixed solvents composed of chloroform-methanol-17% aqueous ammonia (2:1:1) so that they are separable from each other. To separate istamycin A from istamycin B, a mixture of istamycins A and B may be subjected to a chromatographic isolation in a cellulose column developed with mixed solvents composed of n-butanol-pyridine-acetic acid-water (6:4:2:4 by volume) or some analogous mixed solvents, by utilizing the characteristics of istamycins A and B that istamycin A gives a single spot at Rf 0.22 while istamycin B gives a single spot at Rf 0.25 in a cellulose thin layer chromatography developed with the mixed solvents composed of n-butanol-pyridine-acetic acid-water (6:4:2:4). These procedures for the chromatographic isolation may be utilized for the recovery of istamycins as well as for the purification of the isolated istamycin. Istamycin A, B, $A_o$ or $B_o$ may be isolated in a purified state by utilizing the above-mentioned extraction methods and the chromatographic isolating methods, either alone or in a repeated manner, or in combination.

For the recovery of the istamycin complex and for the isolation and purification of each istamycin, the following procedure is preferred: The culture broth of the istamycin-producing strain is adjusted to pH 2.0 by addition of hydrochloric acid and then filtered to give the broth filtrate which is subsequently passed through a column of a cation-exchange resin such as Amberlite IRC-50 ($NH_4^+$ cycle). The resin is washed with water and the adsorbed istamycin is then eluted with 1 N aqueous ammonia. The active fractions of the eluate are combined and concentrated under reduced pressure to give a concentrated solution which is subsequently passed through a column of a cation-exchange resin such as Amberlite CG-50. This resin is washed with water and then with 0.2 N aqueous ammonia, and the adsorbed istamycin is subsequently eluted with 0.4 N aqueous ammonia.

A series of the active fractions containing a substantial amount of istamycin B may be combined and concentrated in vacuo to dryness to give istamycin B as a crude powder. This crude powder is repeatedly subjected to column chromatography on silica gel to give purified istamycin B as a colorless powder.

A series of the active fractions containing a substantial amount of istamycin A as well as some amounts of istamycins $A_o$ and $B_o$ may be combined and concentrated in vacuo to dryness to give a crude powder comprising istamycins A, $A_o$ and $B_o$. This crude powder is then subjected to column chromatography on silica gel developed with the lower phase composed of chloroform-methanol-8.5% aqueous ammonia (2:1:1 by volume).

The active fractions of the eluate which contain solely istamycin $A_o$ are combined and concentrated in vacuo, and the concentrated solution is passed through a column of a cation-exchange resin such as Amberlite CG-50 ($NH_4^+$ cycle), followed by elution of the resin with 0.5 N aqueous ammonia. The active fractions so eluted containing solely istamycin $A_o$ are combined and concentrated in vacuo to dryness to give a colorless crystalline powder of pure istamycin $A_o$.

The active fractions of the eluate from the aforesaid silica gel column chromatography which contain istamycin A are combined and concentrated in vacuo. The concentrated solution so obtained is again subjected to a column chromatography on silica gel, and the active fractions containing solely istamycin A are combined and concentrated to dryness to give a colorless powder of purified istamycin A. Such active fractions of the eluate from the aforesaid silica gel column chromatography which are containing solely istamycin $B_o$ are combined and concentrated in vacuo, and the resultant concentrated solution is subjected to column chromatography on a cation-exchange resin such as Amberlite CS-50 ($NH_4^+$ cycle) and eluted with 0.5 N aqueous ammonia. The active fractions of the eluate containing solely istamycin $B_o$ are combined and concentrated in vacuo to dryness to give a colorless crystalline powder of purified istamycin $B_o$.

From structural studies of istamycins A, B, $A_o$ and $B_o$, it has been found that istamycin $A_o$ is a de-glycyl derivative of istamycin A and that istamycin $B_o$ is a de-glycyl derivative of istamycin B (compare Formulae I and II with Formulae III, IV, V shown hereinbefore). Therefore, istamycin $A_o$ and istamycin $B_o$ of this invention can be converted into istamycin A and istamycin B, respectively, by condensing in a known manner a glycine molecule with the imino group present in the methylamino group at the 4-position of istamycin $A_o$ or istamycin $B_o$. This conversion is valuable as istamycin A and istamycin B have higher antibacterial activities and are much more useful chemotherapeutic agents than istamycin $A_o$ or istamycin $B_o$.

Also, it has been found that istamycin $A_o$ and istamycin $B_o$ can be produced by hydrolyzing istamycin A and istamycin B, respectively, under alkaline conditions. According to a third aspect of this invention, therefore, there is provided a process of producing istamycin $A_o$ from istamycin A or istamycin $B_o$ from istamycin B, which comprises hydrolyzing istamycin A or istamycin B in solution in water under alkaline conditions to produce istamycin $A_o$ or istamycin $B_o$. The alkaline hydrolysis of istamycin A or istamycin B according to the process of the third aspect of the invention may be effected by heating an aqueous solution of istamycin A or istamycin B at a temperature of from about 50° C. to about 110° C. in the presence of an alkali such as an alkali metal or alkaline earth metal hydroxide or carbonate, for example, sodium hydroxide, potassium hydroxide, barium hydroxide or the like. The alkali may be present at a concentration of from about 0.1 to about 4 M. The hydrolysis can be completed in about 1–3 hours. For instance, the hydrolysis of istamycin A or istamycin B may preferably be achieved by heating it in water containing 4 M sodium hydroxide at 100° C. for 1 hour or in water containing 0.5 M barium hydroxide at 100° C. for 3 hours. Under these reaction conditions, the glycosidic linkages of istamycin $A_o$ or istamycin $B_o$ do not break. The alkaline hydrolysis also may be conducted in a culture broth or a broth filtrate containing istamycin A or istamycin B.

The istamycin A and istamycin B of this invention have high antibacterial activity and low toxicity to animals. Accordingly, istamycins A and B are used similarly to other antibiotics known as antibacterial agents, and may be formulated into known pharmaceutical forms and administered in the same manner as known anti-bacterial antibiotic agents. According to a further aspect of this invention, therefore, there is provided a pharmaceutical composition comprising a safe and effective anti-bacterial amount of at least one of istamycin A, istamycin B and acid-addition salts thereof, in combination with a pharmaceutically acceptable carrier. According to another aspect of this invention, there is provided a method for inhibiting bacterial growth which comprises administering an antibacterially effective amount of at least one of istamycin A, istamycin B and acid-addition salts thereof to an animal susceptible to the bacterial growth. It will be appreciated that the actual preferred amounts of the istamycin used will vary according to the particular composition formulated, the mode of application and the particular situs and organism being treated. Many factors which modify the action of the drug will be taken into account by those skilled in the art, for example, age, body weight, sex, diet, time of administration, rate of excretion, drug combinations, reaction sensitivities and severity of the disease. Optimal application rates for a given set of conditions can be ascertained by those skilled in the art using conventional dosage determination tests in view of the above guidelines.

As stated above, *Streptomyces tenjimariensis* SS-939 (FERM-P 4932, ATCC number 31603) is a new microorganism useful to produce the new antibiotics, istamycin and having the microbiological properties described hereinbefore. According to a further aspect of this invention, there is provided as a new and useful microorganism, *Streptomyces tenjimariensis* SS-939 isolated in a substantially pure state and deposited as FERM-P 4932 or ATCC number 31603 and having the characteristics that it produces aerial hyphae which are white in color and which vary gradually to grey with a bluish-green tinge, that the aerial hyphae produce no spirals, the spore surface is smooth, and that the strain shows chromogenicity, utilizes glucose and inositol but does not utilize arabinose, D-xylose, sucrose, rhamnose, raffinose and D-mannitol as the carbon source and is able to produce istamycins A, B, $A_o$ and $B_o$. This SS-939 strain was isolated by incubating a soil sample collected from the sea bottom in the coast of Miura Peninsula in Kanagawa Prefecture, Japan on an MY culture medium comprising 1% maltose, 0.4% yeast extract, 1.5% agar (pH 7.2) with addition of 10 mcg/ml of kanamycin A. Isolation was made after incubation of the above agar medium at 27° C. for 3 days and by picking up mycelia and spores of a colony which was produced on said MY medium. The said mycelia and spores were inoculated to plates of Pridham-Gottlieb culture media (test media for estimation of assimilability of various carbohydrates) each containing 1% of glucose, xylose, arabinose, rhamnose, raffinose or inositol. The novel strain of actinomycetes, *S. tenjimariensis*, was isolated on the basis of its ability to grow on Pridham-Gottlieb culture media utilizing inositol as the sole carbon source.

It is believed that using the preceding description and without further elaboration, one skilled in the art can utilize the concept of this invention to its full extent. The following preferred specific embodiments are, therefore, to be construed as merely illustrative and not limitative of the remainder of the disclosure in any way.

DESCRIPTION OF THE PREFERRED EMBODIMENTS

Example 1

An agar slant culture of *Streptomyces tenjimariensis* SS-939 (FERM-P 4932; ATCC 31603) was inoculated to a liquid culture medium (110 ml, placed in an Erlenmeyer flask of 500 ml capacity) comprising 1.0% starch, 0.2% glucose, 1.0% soybean meal, 0.3% sodium chloride, 0.1% dipotassium hydrogenphosphate and 0.1% magnesium sulfate (7 $H_2O$), followed by cultivation with rotating and shaking at 27° C. for 48 hours to give a seed culture. The resultant seed culture (220 ml) was inoculated into a 30-liter jar fermentor containing 15 liters of a liquid production culture medium comprising 2.0% starch, 0.2% glucose, 2.0% soybean meal, 0.3% sodium chloride, 0.1% dipotassium hydrogenphosphate and 0.1% magnesium sulfate (7 $H_2O$). The fermentation was conducted at 27° C. for 72 hours with aeration (15 liters of air per minute) and agitation (300 r.p.m.).

The culture broths collected from six jar fermentors were combined, adjusted to pH 2.0 by addition of hydrochloric acid and then filtered to give 90 liters of the broth filtrate (potency 2.5 mcg/ml). The broth filtrate was passed through a column (12 liters) of Amberlite IRC-50 ($NH_4^+$ form) (a product of Rohm & Haas Co., U.S.A.) for adsorption of istamycin by the resin. The resin was washed with 24 liters of water and then eluted with 1 N aqueous ammonia. The active fractions of the eluate were combined (3 liters) and concentrated in vacuo to dryness to give 3.51 g of a crude powder (potency 61 mcg/mg).

This crude powder was dissolved in 100 ml of water, and the resulting solution was passed through a column (40 mm in diameter) of 300 ml of an anion-exchange resin, Dowex 1-X4 ($OH^-$ form) (a product of Dow Chemical Co., U.S.A.), followed by development of the column with water. The first portion (200 ml) of the effluent from the column was discarded but the remainder (880 ml) of the effluent was collected and passed into a column (25 mm in diameter) of 150 ml of Amberlite CG-50 ($NH_4^+$ form) for adsorption of istamycin. This cation-exchange resin column was washed with water (300 ml) and subsequently eluted with 900 ml of 0.2 N aqueous ammonia and then with 900 ml of 0.4 N aqueous ammonia. The eluate was collected in 18 ml fractions. Active Fraction Nos. 66–80 were combined and concentrated to dryness under reduced pressure to give 210 mg of a white powder (potency, 460 mcg/mg) comprising istamycins A and B. Fraction Nos. 28–65 were similarly processed to give a crude powder comprising some unidentified antibiotics other than istamycins A, B, $A_o$ and $B_o$.

Example 2

The broth filtrate (150 liters, collected from ten jar fermentors) obtained by fermentation of *Streptomyces tenjimariensis* in the same manner as in Example 1 was passed through a column of 20 liters of Amberlite IRC-50 ($NH_4^+$ form) for adsorption of istamycin. After washing with water (40 liters), the column was eluted with 1 N aqueous ammonia, and the active fractions of the eluate were combined and concentrated to dryness under reduced pressure to give 4.1 g of a crude powder (potency 240 mcg/mg).

This crude powder was dissolved in 20 ml of water, and the resulting aqueous solution was placed into a column (30 mm in diameter) of 200 ml of Dowex 1-X4 ($OH^-$ form), followed by development of the column with water. The first portion (270 ml) of the effluent was discarded and the remainder (270 ml) was collected and then passed through a column (25 mm in diameter) of 150 ml of Amberlite CG-50 ($NH_4^-$ form) for adsorption of istamycin. The resin column was washed with 150 ml of water and then eluted with 900 ml of 0.2 N aqueous ammonia and with 900 ml of 0.4 N aqueous ammonia. The eluate was collected in 18 ml fractions. Fraction Nos. 55–90 were combined and concentrated to dryness under reduced pressure to yield 980 mg of a white powder (potency, 940 mcg/mg) comprising istamycins A and B.

Example 3

The white powder (980 mg, potency 940 mcg/mg) comprising istamycins A and B obtained in Example 2 was taken up in 15 ml of a mixture of n-butanol-pyridine-acetic acid-water (6:4:2:2 by volume), and the resulting solution was placed into a column (25 mm in diameter) of 60 g of cellulose powder (Avicel, a product of Funakoshi Yakuhin Co.) for adsorption of istamycin. The cellulose column was developed first with 1200 ml of a mixture of n-butanol-pyridine-acetic acid-water (6:4:2:2 by volume) and subsequently with 600 ml of a mixture of n-butanol-pyridine-acetic acid-water (6:4:2:4 by volume). The eluate was collected in 10 ml fractions. Fraction Nos. 45–74 contained solely istamycin B, Fraction Nos. 114–154 contained solely istamycin A and Fraction Nos. 75–113 contained a mixture of istamycins A and B.

Fraction Nos. 45–74 were combined and concentrated to dryness under reduced pressure to give a powder, which was then dissolved in 5 ml of water. The aqueous solution of istamycin B so obtained was passed into a column of 25 ml of Amberlite CG-50 ($NH_4^+$ form) for adsorption of istamycin B. After washing with 25 ml of water, the resin column was eluted with 0.4 N aqueous ammonia. The active fractions (totalling 40 ml) of the eluate were concentrated to dryness under reduced pressure to yield 15.3 mg of a powder of pure istamycin B (potency 3170 mcg/mg).

Fraction Nos. 114–154 were combined and concentrated to dryness under reduced pressure to give a powder, which was then dissolved in 5 ml of water. The solution of istamycin A in water so obtained was passed through a column of 25 ml of Amberlite CG-50 ($NH_4^+$ form) for adsorption of istamycin A. After washing with 25 ml of water, the column was eluted with 0.4 N aqueous ammonia. The active fractions (totalling 45 ml) of the eluate were concentrated to dryness under reduced pressure to yield 50 mg of a powder of pure istamycin A (potency 1000 mcg/mg).

Example 4

An agar slant culture of *Streptomyces tenjimariensis* SS-939 (FERM-P 4932; ATCC 31603) was inoculated to a liquid culture medium (110 ml, placed in an Erlenmeyer flask of 500 ml capacity) comprising 1.0% starch, 0.2% glucose, 1.0% soybean meal, 0.3% sodium chloride, 0.1% dipotassium hydrogenphosphate and 0.1% magnesium sulfate (7 $H_2O$). The cultivation was conducted at 27° C. for 48 hours with shaking and rotating, to give a seed culture. This seed culture (220 ml) was inoculated into 30-liter jar fermentors each containing 15 liters of a liquid production culture medium comprising 2.0% starch, 0.2% glucose, 2.0% soybean meal, 0.2% sodium palmitate, 0.3% sodium chloride, 0.1% dipotassium hydrogenphosphate and 0.1% magnesium sulfate (7 $H_2O$). The fermentation was conducted at 27° C. for 72 hours with aeration (15 liters of air per minute) and agitation (300 r.p.m.).

The culture broth so produced were collected from ten jar-fermentors, adjusted to pH 2.0 by addition of hydrochloric acid and then filtered to give 150 liters of broth filtrate (potency, 6 mcg/mg). This broth filtrate was passed through a column of 12 liters of Amberlite IRC-50 ($NH_4^+$ form) for adsorption of istamycin. After washing with 24 liters of water, the resin column was eluted with 1 N aqueous ammonia. The active fractions (totalling 5.6 liters) of the eluate were combined and concentrated under reduced pressure. The resulting concentrated solution was placed into a column of 200 ml of Amberlite CG-50 ($NH_4^+$ form) for adsorption of istamycin. After washing with 200 ml of water, the resin column was washed with 1200 ml of 0.2 N aqueous ammonia and then eluted with 1200 ml of 0.4 N aqueous ammonia. The eluate was collected in 18 ml fractions.

Fraction Nos. 80–106 were combined and concentrated to dryness under reduced pressure to give 240 mg of a crude powder of istamycin B (potency, 380 mcg/mg). This crude powder was repeatedly subjected to column chromatography on silica gel developed with the lower phase of a mixture of chloroform-methanol-8.5% aqueous ammonia (2:1:1) until there was afforded a purified, white powder of istamycin B of a potency 1350 mcg/mg. Yield 25 mg.

Fraction Nos. 107–124 were combined and concentrated to dryness under reduced pressure to give 380 mg of a crude powder (potency, 180 mcg/mg) comprising istamycins A, $A_o$ and $B_o$. This crude powder was subjected to column chromatography using a column of 38 g of silica gel (60, a product of E. Merck Co., Germany) and developed with the lower phase of a mixture of chloroform-methanol-8.5% aqueous ammonia (2:1:1 by volume). The eluate from the silica gel column was collected in 5 ml fractions.

Fraction Nos. 54–61 were combined and concentrated under reduced pressure, and then placed into a column of 3 ml of Amberlite CG-50 ($NH_4^+$ form) for adsorption of istamycin $A_o$. The Amberlite column was eluted with 0.5 N aqueous ammonia, and the active fractions of the effluent were concentrated to dryness under reduced pressure to yield a colorless crystalline powder of pure istamycin $A_o$ (potency, 5 mcg/mg). Yield 25 mg.

Fraction Nos. 65–76 were combined and concentrated under reduced pressure, and then subjected to column chromatography using a column of 10 g of silica gel and developed with the lower phase of a mixture of chloroform-methanol-8.5% aqueous ammonia (2:1:1) for the purification of istamycin A. In this way, a colorless powder of pure istamycin A (potency, 1000 mcg/mg) was obtained in a yield of 23 mg.

Fraction Nos. 77–90 were combined and concentrated under reduced pressure, and then passed into a column of 3 ml of Amberlite CG-50 ($NH_4^+$ form) for adsorption of istamycin $B_o$. This column was eluted with 0.5 N aqueous ammonia, and the active fractions of the eluate were concentrated to dryness under reduced pressure to give a colorless crystalline powder of pure istamycin $B_o$ (potency, 10 mcg/mg). Yield 18 mg.

Example 5

This Example and the following Examples illustrate the production of istamycin $A_o$ or $B_o$ from istamycin A or istamycin B by alkaline hydrolysis.

A solution of 20 mg of istamycin A in 2 ml of water was mixed with 300 mg of barium hydroxide [$Ba(OH)_2 \cdot 8H_2O$]. The mixture was heated at 100° C. for 3 hours in a sealed tube to effect the alkaline hydrolysis of istamycin A. The reaction mixture was neutralized by the addition of solidified carbon dioxide and then filtered. The filtrate was passed through a column of 3 ml of Amberlite CG-50 ($NH_4^+$ form), and the column was eluted with 0.5 N aqueous ammonia. The active fractions of the eluate were concentrated to dryness under reduced pressure to yield 16 mg of a colorless crystalline powder of pure istamycin $A_o$.

Istamycin B (20 mg) was subjected to alkaline hydrolysis in the same manner as stated just above. A colorless crystalline powder of pure istamycin $B_o$ was afforded in yield of 15 mg.

Example 6

An agar slant culture of *Streptomyces tenjimariensis* SS-939 (FERM-P 4932) was inoculated to a liquid culture medium (50 liters) comprising 1.0% starch, 0.2% glucose, 1.0% soybean meal, 0.3% sodium chloride, 0.1% dipotassium hydrogenphosphate and 0.1% magnesium sulfate (7 $H_2O$) (pH 7.0) placed in a stainless steel fermentation tank of 100 liters capacity. The fermentation was conducted at 28° C. for 24 hours with aeration (50 liters of air per minute) and agitation (200 r.p.m.) to produce a seed culture. A portion (20 liters) of the resulting seed culture was inoculated to a stainless steel fermentation tank of 2-ton capacity containing 1000 liters of a liquid culture medium comprising 4.0% starch, 0.4% glucose, 5.0% wheat germ, 0.6% calcium carbonate and 0.3% sodium chloride (pH 7.0), followed by fermentation at 28° C. for 108 hours with aeration (800 liters of air per minute) and agitation (280 r.p.m.).

The fermentation broth (pH 7.3) so obtained was adjusted to pH 2.0 by addition of hydrochloric acid and then filtered. The filtrate was neutralized with aqueous sodium hydroxide to afford 850 liters of a broth filtrate (pH 6.2, potency 105 mcg/ml). This broth filtrate was passed into a column of 55 liters of Amberlite IRC-50 ($NH_4^+$ form) for adsorption of istamycin. After washing with 300 liters of water, the column was eluted with 1.1 N aqueous ammonia. The first portion (38 liters) of the effluent was discarded and the remainder (188 liters) was collected and concentrated to a volume of 2.8 liters under reduced pressure.

The concentrated solution so obtained was mixed with 475.2 g of barium hydroxide [$Ba(OH)_2 \cdot 8H_2O$], followed by heating at 110° C. for 3 hours under reflux to effect the alkaline hydrolysis of istamycins A and B. The reaction mixture was neutralized (to pH 7.2) by addition of 1960 ml of 2 N sulfuric acid and then filtered. The filtrate was passed through a column of 15 liters of Amberlite CG-50 ($NH_4^+$ form) for adsorption of istamycin. After washing with 45 liters of water, the column was eluted successively with aqueous solutions of ammonia at varying concentrations as indicated below, while the eluate was collected in 3-liter fractions.

Fraction Nos. 1–20: with 60 liters of 0.10 N aqueous ammonia

Fraction Nos. 21–40: with 60 liters of 0.15 N aqueous ammonia

Fraction Nos. 41–60: with 60 liters of 0.19 N aqueous ammonia

Fraction Nos. 61–80: with 60 liters of 0.26 N aqueous ammonia

Fraction Nos. 81–100: with 60 liters of 0.27 N aqueous ammonia

Fraction Nos. 101–120: with 60 liters of 0.32 N aqueous ammonia

Fraction Nos. 121–140: with 60 liters of 0.35 N aqueous ammonia

Fraction Nos. 141–160: with 60 liters of 0.43 N aqueous ammonia

Fraction Nos. 161–180: with 30 liters of 1.00 N aqueous ammonia

Fraction Nos. 82–104 were combined and concentrated to dryness under reduced pressure to give 38.05 g of a crude powder comprising istamycin $A_o$. Fraction Nos. 105–134 were combined and concentrated to dryness under reduced pressure to afford 19.19 g of a crude powder comprising istamycin $B_o$.

Example 7

The crude istamycin $A_o$ (2.0 g) obtained in Example 6 was purified by column chromatography using 180 g of silica gel and developing with the lower phase of a mixture of chloroform-methanol-8.5% aqueous ammonia (2:1:1 by volume) while the eluate was collected in 25-ml fractions. Active Fraction Nos. 65-104 were combined and concentrated to dryness under reduced pressure to give a colorless crystalline powder of pure istamycin $A_o$. Yield 586 mg.

The crude istamycin $B_o$ (2.0 g) obtained in Example 6 was purified by column chromatography on silica gel in the same manner as stated just above, except that the eluate was collected in 23-ml fractions. Active Fraction Nos. 73-170 were combined and concentrated to dryness under reduced pressure to afford a colorless crystalline powder of pure istamycin $B_o$. Yield 1369 mg.

We claim:

1. The new compound, istamycin, which is selected from istamycin A of the formula

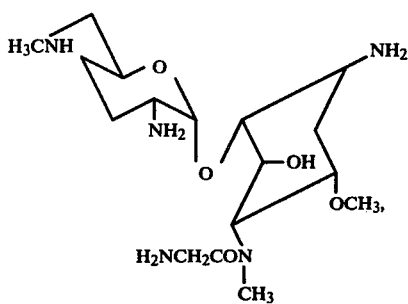

istamycin B of the formula

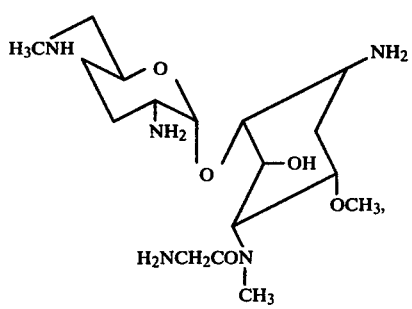

istamycin $A_o$ of the formula

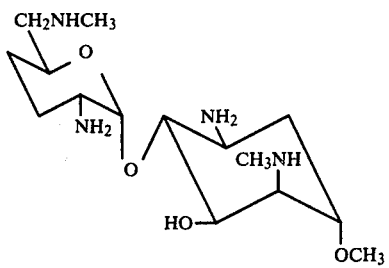

or

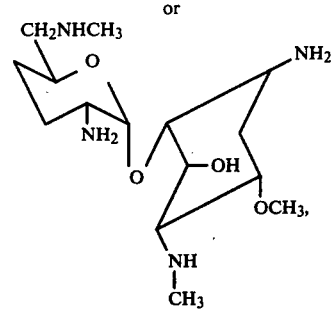

and istamycin $B_o$ of the formula

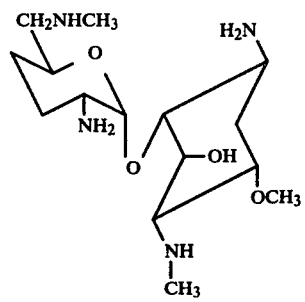

and mixtures thereof, or a nontoxic pharmaceutically acceptable acid-addition salt thereof.

2. The compound of claim 1 which is istamycin A or a non-toxic pharmaceutically acceptable acid-addition salt thereof.

3. The compound of claim 1 which is istamycin B or a non-toxic pharmaceutically acceptable acid-addition salt thereof.

4. The compound of claim 1 which is istamycin $A_o$ or a non-toxic pharmaceutically acceptable acid-addition salt thereof.

5. The compound of claim 1 which is istamycin $B_o$ or a non-toxic pharmaceutically acceptable acid-addition salt thereof.

6. A pharmaceutical composition comprising a safe and effective antibacterial amount of at least one of istamycin A, istamycin B and nontoxic pharmaceutically acceptable acid-addition salts thereof, in combination with a pharmaceutically acceptable carrier.

7. A method for inhibiting bacterial growth in an animal susceptible to said bacterial growth which comprises administering to said animal an antibacterially effective amount of at least one of istamycin A, istamycin B and nontoxic pharmaceutically acceptable acid-addition salts thereof.

* * * * *

UNITED STATES PATENT AND TRADEMARK OFFICE
CERTIFICATE OF CORRECTION

PATENT NO. : 4,296,106

DATED : October 20, 1981

INVENTOR(S) : Hamao Umezawa et al.

It is certified that error appears in the above—identified patent and that said Letters Patent is hereby corrected as shown below:

In Column 5, at approximately Line 47, the word -- or -- should appear between structure III and structure IV.

In Column 7 (Table 1), the fifteenth and sixteenth entries in that table should be combined to read as follows:

-- Escherichia coli K-12 C600 R135      >50      25 -- .

In Column 7 (Table 1), the entry reading "Shigella sonnei S11756" should read -- Shigella sonnei SJ11756 -- .

In Column 7 (Table 1), the entry reading "Salmonella enteridtidis 1891" should read -- Salmonella enteritidis 1891 -- .

Signed and Sealed this

Twenty-second Day of December 1981

[SEAL]

Attest:

GERALD J. MOSSINGHOFF

Attesting Officer    Commissioner of Patents and Trademarks